(12) United States Patent
Farwick et al.

(10) Patent No.: US 6,759,224 B2
(45) Date of Patent: Jul. 6, 2004

(54) NUCLEOTIDE SEQUENCES WHICH CODE FOR THE SAHH GENE

(75) Inventors: Mike Farwick, Bielefeld (DE); Klaus Huthmacher, Gelnhausen (DE); Jennifer Brehme, Bielefeld (DE); Walter Pfefferle, Halle (DE); Michael Binder, Steinhagen (DE); Dieter Greissinger, Niddatal (DE); Georg Thierbach, Bielefeld (DE)

(73) Assignee: Degussa AG, Duesseldorf (DE)

( * ) Notice: Subject to any disclaimer, the term of this patent is extended or adjusted under 35 U.S.C. 154(b) by 182 days.

(21) Appl. No.: 09/919,854

(22) Filed: Aug. 2, 2001

(65) Prior Publication Data

US 2003/0100080 A1 May 29, 2003

Related U.S. Application Data

(60) Provisional application No. 60/294,277, filed on May 31, 2001.

(30) Foreign Application Priority Data

Sep. 9, 2000 (DE) .......................................... 100 44 706
Feb. 28, 2001 (DE) .......................................... 101 09 685

(51) Int. Cl.$^7$ ................................................ C12N 9/14
(52) U.S. Cl. ...................... 435/195; 435/69.1; 435/183; 435/252.3; 435/252.32; 435/320.1; 536/23.2
(58) Field of Search ............................... 435/69.1, 183, 435/195, 252.3, 252.32, 320.1; 536/23.2

(56) References Cited

U.S. PATENT DOCUMENTS

| 3,729,381 A | 4/1973 | Nakayama et al. ........... 195/96 |
| 2003/0049804 A1 | 3/2003 | Pompejus et al. | |

FOREIGN PATENT DOCUMENTS

| DE | 38 234 51 | 1/1990 |
| EP | 0 287 152 | 10/1988 |
| EP | 0 435 132 | 7/1991 |
| EP | 1108790 A2 | 6/2001 |
| WO | WO 01/00802 | 1/2001 |
| WO | WO 01/00804 | 1/2001 |
| WO | WO 01/00843 | 1/2001 |
| WO | WO 01/00845 | 1/2001 |
| WO | WO 01/00847 | 1/2001 |
| WO | WO 01/66573 | 9/2001 |

OTHER PUBLICATIONS

Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*
Pawar et al. Accession AF262755. May 30, 2000.*
S. T. Cole, et al., Database EMBL Online!, MTY20B11, Acc. No: Z95121, XP–002183842, pp. 1–25, "Deciphering the Biology of Mycobacterium Tuberculosis from the Complete Genome Sequence", May 6, 1997.
L. Eggeling, et al., Appl. Microbiol. Biotechnol., vol. 49, No. 1, XP–000918549. pp. 24–30. "Improved L–Lysine Yield with *Corynebacterium glutamicum*: Use of DAPA Resulting in Increased Flux Combined with Growth Limitation", 1998.
H. Sahm, et al., Annals of the New York Academy of Sciences, vol. 782, XP–000943151, pp. 25–39, "Construction of L–Lysine–, L–Threonine–, or L–Isoleucine–Overproducing Strains of *Corynebacterium glutamicum*", 1996.

* cited by examiner

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

An isolated polynucleotide comprising a polynucleotide sequence selected from the group consisting of
a) polynucleotide which is at least 70% identical to a polynucleotide that codes for a polypeptide which comprises the amino acid sequence of SEQ ID No. 2,
b) polynucleotide which codes for a polypeptide that comprises an amino acid sequence which is at least 70% identical to the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c),
and a process for the fermentative preparation of L–amino acids using coryneform bacteria, in which at least the sahH gene is present in enhanced form, and the use of polynucleotides which contain the sequences according to the invention as hybridization probes.

47 Claims, 2 Drawing Sheets

Figure 1: Map of the E. coli-C. glutamicum shuttle vectors pEC-XK99E

Figure 2: Map of the plasmid pEC-XK99EsahHa1ex

SEQUENCE LISTING

```
<160> NUMBER OF SEQ ID NOS: 4

<210> SEQ ID NO 1
<211> LENGTH: 1939
<212> TYPE: DNA
<213> ORGANISM: Corynebacterium glutamicum
<220> FEATURE:
<221> NAME/KEY: CDS
<222> LOCATION: (227)..(1720)
<223> OTHER INFORMATION:

<400> SEQUENCE: 1
```

-continued

```
tcgcggccat catgtttggc gctccatatt ctgcgggcca ggtgctggag aattacccat      60
ttatccgcga actcgtcggt gagggctctg aagctcttcg cggtgctgca gcgcaggttt     120
tggaagaggc agatgtggaa tatgacctcg aagcttattt agaggccctc aactagccct     180
ccactaaaca gcttcaatca attcggtgtc cactccaaca tgtaga gtg gtg cgc        235
                                                  Val Val Arg
                                                   1 gtt aaa aaa gtt ttc cta att ttc att ttc tta aaa gga gct cgc cag       283
Val Lys Lys Val Phe Leu Ile Phe Ile Phe Leu Lys Gly Ala Arg Gln
  5              10                  15 gac atg gca cag gtt atg gac ttc aag gtt gcc gat ctt tca cta gca       331
Asp Met Ala Gln Val Met Asp Phe Lys Val Ala Asp Leu Ser Leu Ala
 20              25                  30                  35 gag gca gga cgt cac cag att cgt ctt gca gag tat gag atg cca ggt       379
Glu Ala Gly Arg His Gln Ile Arg Leu Ala Glu Tyr Glu Met Pro Gly
                 40                  45                  50 ctc atg cag ttg cgc aag gaa ttc gca gac gag cag cct ttg aag ggc       427
Leu Met Gln Leu Arg Lys Glu Phe Ala Asp Glu Gln Pro Leu Lys Gly
             55                  60                  65 gcc cga att gct ggt tct atc cac atg acg gtc cag acc gcc gtg ctt       475
Ala Arg Ile Ala Gly Ser Ile His Met Thr Val Gln Thr Ala Val Leu
         70                  75                  80 att gag acc ctc act gct ttg ggc gct gag gtt cgt tgg gct tcc tgc       523
Ile Glu Thr Leu Thr Ala Leu Gly Ala Glu Val Arg Trp Ala Ser Cys
 85                  90                  95 aac att ttc tcc acc cag gat gag gct gca gcg gct atc gtt gtc ggc       571
Asn Ile Phe Ser Thr Gln Asp Glu Ala Ala Ala Ala Ile Val Val Gly
100                 105                 110                 115 tcc ggc acc gtc gaa gag cca gct ggt gtt cca gta ttc gcg tgg aag       619
Ser Gly Thr Val Glu Glu Pro Ala Gly Val Pro Val Phe Ala Trp Lys
                120                 125                 130 ggt gag tca ctg gag gag tac tgg tgg tgc atc aac cag atc ttc agc       667
Gly Glu Ser Leu Glu Glu Tyr Trp Trp Cys Ile Asn Gln Ile Phe Ser
            135                 140                 145 tgg ggc gat gag ctg cca aac atg atc ctc gac gac ggc ggt gac gcc       715
Trp Gly Asp Glu Leu Pro Asn Met Ile Leu Asp Asp Gly Gly Asp Ala
        150                 155                 160 acc atg gct gtt att cgc ggt cgc gaa tac gag cag gct ggt ctg gtt       763
Thr Met Ala Val Ile Arg Gly Arg Glu Tyr Glu Gln Ala Gly Leu Val
    165                 170                 175 cca cca gca gag gcc aac gat tcc gat gag tac atc gca ttc ttg ggc       811
Pro Pro Ala Glu Ala Asn Asp Ser Asp Glu Tyr Ile Ala Phe Leu Gly
180                 185                 190                 195 atg ctg cgt gag gtt ctt gct gca gag cct ggc aag tgg ggc aag atc       859
Met Leu Arg Glu Val Leu Ala Ala Glu Pro Gly Lys Trp Gly Lys Ile
                200                 205                 210 gct gag gcc gtt aag ggt gtc acc gag gaa acc acc acc ggt gtg cac       907
Ala Glu Ala Val Lys Gly Val Thr Glu Glu Thr Thr Thr Gly Val His
            215                 220                 225 cgc ctg tac cac ttc gct gaa gaa ggc gtg ctg cct ttc cca gcg atg       955
Arg Leu Tyr His Phe Ala Glu Glu Gly Val Leu Pro Phe Pro Ala Met
        230                 235                 240 aac gtc aac gac gct gtc acc aag tcc aag ttt gat aac aag tac ggc      1003
Asn Val Asn Asp Ala Val Thr Lys Ser Lys Phe Asp Asn Lys Tyr Gly
    245                 250                 255 acc cgc cac tcc ctg atc gac ggc atc aac cgc gcc act gac atg ctc      1051
Thr Arg His Ser Leu Ile Asp Gly Ile Asn Arg Ala Thr Asp Met Leu
260                 265                 270                 275
```

-continued

| | | |
|---|---|---|
| atg ggc ggc aag aac gtg ctt gtc tgc ggt tac ggc gat gtc ggc aag<br>Met Gly Gly Lys Asn Val Leu Val Cys Gly Tyr Gly Asp Val Gly Lys<br>280 285 290 | | 1099 |
| ggc tgc gct gag gct ttc gac ggc cag ggc gct cgc gtc aag gtc acc<br>Gly Cys Ala Glu Ala Phe Asp Gly Gln Gly Ala Arg Val Lys Val Thr<br>295 300 305 | | 1147 |
| gaa gct gac cca atc aac gct ctt cag gct ctg atg gat ggc tac tct<br>Glu Ala Asp Pro Ile Asn Ala Leu Gln Ala Leu Met Asp Gly Tyr Ser<br>310 315 320 | | 1195 |
| gtg gtc acc gtt gat gag gcc atc gag gac gcc gac atc gtg atc acc<br>Val Val Thr Val Asp Glu Ala Ile Glu Asp Ala Asp Ile Val Ile Thr<br>325 330 335 | | 1243 |
| gcg acc ggc aac aag gac atc att tcc ttc gag cag atg ctc aag atg<br>Ala Thr Gly Asn Lys Asp Ile Ile Ser Phe Glu Gln Met Leu Lys Met<br>340 345 350 355 | | 1291 |
| aag gat cac gct ctg ctg ggc aac atc ggt cac ttt gat aat gag atc<br>Lys Asp His Ala Leu Leu Gly Asn Ile Gly His Phe Asp Asn Glu Ile<br>360 365 370 | | 1339 |
| gat atg cat tcc ctg ttg cac cgc gac gac gtc acc cgc acc acg atc<br>Asp Met His Ser Leu Leu His Arg Asp Asp Val Thr Arg Thr Thr Ile<br>375 380 385 | | 1387 |
| aag cca cag gtc gac gag ttc acc ttc tcc acc ggt cgc tcc atc atc<br>Lys Pro Gln Val Asp Glu Phe Thr Phe Ser Thr Gly Arg Ser Ile Ile<br>390 395 400 | | 1435 |
| gtc ctg tcc gaa ggt cgc ctg ttg aac ctt ggc aac gcc acc gga cac<br>Val Leu Ser Glu Gly Arg Leu Leu Asn Leu Gly Asn Ala Thr Gly His<br>405 410 415 | | 1483 |
| cca tca ttt gtc atg tcc aac tct ttc gcc gat cag acc att gcg cag<br>Pro Ser Phe Val Met Ser Asn Ser Phe Ala Asp Gln Thr Ile Ala Gln<br>420 425 430 435 | | 1531 |
| atc gaa ctg ttc caa aac gaa gga cag tac gag aac gag gtc tac cgt<br>Ile Glu Leu Phe Gln Asn Glu Gly Gln Tyr Glu Asn Glu Val Tyr Arg<br>440 445 450 | | 1579 |
| ctg cct aag gtt ctc gac gaa aag gtg gca cgc atc cac gtt gag gct<br>Leu Pro Lys Val Leu Asp Glu Lys Val Ala Arg Ile His Val Glu Ala<br>455 460 465 | | 1627 |
| ctc ggc ggt cag ctc acc gaa ctg acc aag gag cag gct gag tac atc<br>Leu Gly Gly Gln Leu Thr Glu Leu Thr Lys Glu Gln Ala Glu Tyr Ile<br>470 475 480 | | 1675 |
| ggc gtt gac gtt gca ggc cca ttc aag ccg gag cac tac cgc tac<br>Gly Val Asp Val Ala Gly Pro Phe Lys Pro Glu His Tyr Arg Tyr<br>485 490 495 | | 1720 |
| taatgattgt cagcattgag ggaatcgacg gcgccggcaa aaacaccctg gtttcggcat | | 1780 |
| taacgcaggt tattgatgca aaagtccttg cattcccacg ttatgaaacc tcgattcacg | | 1840 |
| cccaattggc cgcggaagca ctccacggcc gcatgggcga cctcaccgac agcgcctacg | | 1900 |
| ccatggccac gcttttcgcc ctcgaccgcc acttcgcga | | 1939 |

<210> SEQ ID NO 2
<211> LENGTH: 498
<212> TYPE: PRT
<213> ORGANISM: Corynebacterium glutamicum

<400> SEQUENCE: 2

Val Val Arg Val Lys Lys Val Phe Leu Ile Phe Ile Phe Leu Lys Gly
1               5                   10                  15

Ala Arg Gln Asp Met Ala Gln Val Met Asp Phe Lys Val Ala Asp Leu
            20                  25                  30

Ser Leu Ala Glu Ala Gly Arg His Gln Ile Arg Leu Ala Glu Tyr Glu

```
                35                    40                    45
Met Pro Gly Leu Met Gln Leu Arg Lys Glu Phe Ala Asp Glu Gln Pro
 50                      55                      60
Leu Lys Gly Ala Arg Ile Ala Gly Ser Ile His Met Thr Val Gln Thr
 65                      70                      75                      80
Ala Val Leu Ile Glu Thr Leu Thr Ala Leu Gly Ala Glu Val Arg Trp
                 85                      90                      95
Ala Ser Cys Asn Ile Phe Ser Thr Gln Asp Glu Ala Ala Ala Ala Ile
                100                     105                     110
Val Val Gly Ser Gly Thr Val Glu Glu Pro Ala Gly Val Pro Val Phe
                115                     120                     125
Ala Trp Lys Gly Glu Ser Leu Glu Glu Tyr Trp Trp Cys Ile Asn Gln
130                     135                     140
Ile Phe Ser Trp Gly Asp Glu Leu Pro Asn Met Ile Leu Asp Asp Gly
145                     150                     155                     160
Gly Asp Ala Thr Met Ala Val Ile Arg Gly Arg Glu Tyr Glu Gln Ala
                165                     170                     175
Gly Leu Val Pro Pro Ala Glu Ala Asn Asp Ser Asp Glu Tyr Ile Ala
                180                     185                     190
Phe Leu Gly Met Leu Arg Glu Val Leu Ala Ala Glu Pro Gly Lys Trp
                195                     200                     205
Gly Lys Ile Ala Glu Ala Val Lys Gly Val Thr Glu Glu Thr Thr Thr
                210                     215                     220
Gly Val His Arg Leu Tyr His Phe Ala Glu Glu Gly Val Leu Pro Phe
225                     230                     235                     240
Pro Ala Met Asn Val Asn Asp Ala Val Thr Lys Ser Lys Phe Asp Asn
                245                     250                     255
Lys Tyr Gly Thr Arg His Ser Leu Ile Asp Gly Ile Asn Arg Ala Thr
                260                     265                     270
Asp Met Leu Met Gly Gly Lys Asn Val Leu Val Cys Gly Tyr Gly Asp
                275                     280                     285
Val Gly Lys Gly Cys Ala Glu Ala Phe Asp Gly Gln Gly Ala Arg Val
                290                     295                     300
Lys Val Thr Glu Ala Asp Pro Ile Asn Ala Leu Gln Ala Leu Met Asp
305                     310                     315                     320
Gly Tyr Ser Val Val Thr Val Asp Glu Ala Ile Glu Asp Ala Asp Ile
                325                     330                     335
Val Ile Thr Ala Thr Gly Asn Lys Asp Ile Ile Ser Phe Glu Gln Met
                340                     345                     350
Leu Lys Met Lys Asp His Ala Leu Leu Gly Asn Ile Gly His Phe Asp
                355                     360                     365
Asn Glu Ile Asp Met His Ser Leu Leu His Arg Asp Asp Val Thr Arg
                370                     375                     380
Thr Thr Ile Lys Pro Gln Val Asp Glu Phe Thr Phe Ser Thr Gly Arg
385                     390                     395                     400
Ser Ile Ile Val Leu Ser Glu Gly Arg Leu Leu Asn Leu Gly Asn Ala
                405                     410                     415
Thr Gly His Pro Ser Phe Val Met Ser Asn Ser Phe Ala Asp Gln Thr
                420                     425                     430
Ile Ala Gln Ile Glu Leu Phe Gln Asn Glu Gly Gln Tyr Glu Asn Glu
                435                     440                     445
Val Tyr Arg Leu Pro Lys Val Leu Asp Glu Lys Val Ala Arg Ile His
450                     455                     460
```

```
Val Glu Ala Leu Gly Gly Gln Leu Thr Glu Leu Thr Lys Glu Gln Ala
465                 470                 475                 480

Glu Tyr Ile Gly Val Asp Val Ala Gly Pro Phe Lys Pro Glu His Tyr
                485                 490                 495

Arg Tyr

<210> SEQ ID NO 3
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 3 gtggtaccttcggtgtccactccaacat                                     28

<210> SEQ ID NO 4
<211> LENGTH: 28
<212> TYPE: DNA
<213> ORGANISM: ARTIFICIAL SEQUENCE
<220> FEATURE:
<223> OTHER INFORMATION: SYNTHETIC DNA

<400> SEQUENCE: 4 catctagataggcgctgtcggtgaggtc                                     28
```

NUCLEOTIDE SEQUENCES WHICH CODE FOR THE SAHH GENE

BACKGROUND OF THE INVENTION

1. Field of the Invention

The invention provides nucleotide sequences from coryneform bacteria which code for the sahH gene and a process for the fermentative preparation of amino acids using bacteria in which the sahH gene is enhanced.

2. Description of the Related Art

L-Amino acids, in particular L-lysine and L-methionine, are used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation process. Improvements to the process can relate to fermentation measures, such as, stirring and supply of oxygen, or to the composition of the nutrient media, such as, the sugar concentration during the fermentation, or to the working up of the product by, for example, ion exchange chromatography, or to the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and produce amino acids are obtained in this manner.

Recombinant DNA techniques have also been employed for some years for improving Corynebacterium strains which produce L-amino acids, by amplifying individual amino acid biosynthesis genes and investigating their effect on amino acid production.

SUMMARY OF THE INVENTION

One object of the present invention is to provide new measures for improved fermentative preparation of amino acids.

Where L-amino acids or amino acids are mentioned in the following, this means one or more amino acid, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine and L-methionine are particularly preferred.

When L-lysine or lysine are mentioned in the following, not only the bases but also the salts, such as e.g. lysine monohydrochloride or lysine sulfate, are meant by this.

When L-methionine or methionine are mentioned in the following, the salts, such as methionine hydrochloride or methionine sulfate are also meant by this.

The invention provides an isolated polynucleotide from coryneform bacteria, comprising a polynucleotide sequence which codes for the sahH gene, chosen from the group consisting of a) polynucleotide which is at least 70% identical to a polynucleotide that codes for a polypeptide which comprises the amino acid sequence of SEQ ID No. 2, b) polynucleotide which codes for a polypeptide that comprises an amino acid sequence which is at least 70% identical to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), and the corresponding polypeptide having the enzytomatic activity of adenosyl homocysteinase.

The invention also provides the above-mentioned polynucleotides, as DNA which is capable of replication, comprising:

(i) the nucleotide sequence shown in SEQ ID No. 1, or (ii) at least one sequence which corresponds to sequence (i) within the range of the degeneration of the genetic code, or (iii) at least one sequence which hybridizes with the sequence complementary to sequence (i) or (ii), and optionally (iv) sense mutations of neutral function in (i).

The invention also provides a polynucleotide, in particular DNA, which is capable of replication and comprises the nucleotide sequence as shown in SEQ ID No. 1;

a polynucleotide that codes for a polypeptide which comprises the amino acid sequence as shown in SEQ ID No. 2;

a vector containing the polynucleotide according to the invention, in particular a shuttle vector or plasmid vector, and coryneform bacteria which contain the vector or in which the sahH gene is enhanced.

The invention also provides polynucleotides which are obtained by screening a corresponding gene library of a coryneform bacterium, which comprises the complete gene or parts thereof, by means of hybridization with a probe which comprises the sequence of the polynucleotide according to the invention according to SEQ ID No.1 or a fragment thereof, and isolation of the polynucleotide sequence mentioned.

DETAILED DESCRIPTION OF THE PREFERRED EMBODIMENTS

Polynucleotides according to the invention are suitable as hybridization probes for RNA, cDNA and DNA, in order to isolate, in the full length, nucleic acids or polynucleotides or genes which code for adenosyl homocysteinase or to isolate those nucleic acids or polynucleotides or genes which have a high similarity or homology of sequence with that of the sahH gene.

Polynucleotides according to the invention are furthermore suitable as primers with the aid of which DNA of genes that code for adenosyl homocysteinase can be prepared by the polymerase chain reaction (PCR).

Such oligonucleotides that serve as probes or primers comprise at least 30, preferably at least 20, very particularly at least 15 successive nucleotides. Oligonucleotides which have a length of at least 40 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70%, preferably at least 80% and in particular at least 90% to 95% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of adenosyl homocysteinase, and also those which are at least 70%, preferably at least 80% and in particular at least 90% to 95% identical to the polypeptide according to SEQ ID No. 2 and have the activity mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using coryneform bacteria which in particular already produce amino acids and in which the nucleotide sequences which code for the sahH gene are enhanced, in particular over-expressed.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on the starting microorganism.

The microorganisms which the present invention provides can produce L-amino acids from glucose, sucrose, lactose, fructose, maltose, molasses, starch, cellulose or from glycerol and ethanol. They can be representatives of coryneform bacteria, in particular of the genus Corynebacterium. Of the genus Corynebacterium, there may be mentioned in particular the species *Corynebacterium glutamicum,* which is known among experts for its ability to produce L-amino acids.

Suitable strains of the genus Corynebacterium, in particular of the species *Corynebacterium glutamicum* (*C. glutamicum*), are in particular the known wild-type strains

*Corynebacterium glutamicum* ATCC13032

*Corynebacterium acetoglutamicum* ATCC15806

*Corynebacterium acetoacidophilum* ATCC13870

*Corynebacterium thermoaminogenes* FERM BP-1539

*Corynebacterium melassecola* ATCC17965

*Brevibacterium flavum* ATCC14067

*Brevibacterium lactofermentum* ATCC13869 and

*Brevibacterium divaricatum* ATCC14020 and L-amino acid-producing mutants or strains prepared therefrom.

The new sahH gene from *C. glutamicum* which codes for the enzyme adenosyl homocysteinase (EC 3.3.1.1.) has been isolated.

To isolate the sahH gene or also other genes of *C. glutamicum,* a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326) (1992)) in turn describe a gene library of *C. glutamicum* ATCC13032 using the cosmid pHC79 (Hohn and Collins, Gene 11, 291–298 (1980)).

To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649). The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be investigated with known algorithms or sequence analysis programs, such as that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* which codes for the sahH gene and which, as SEQ ID No. 1, is a constituent of the present invention has been found. The amino acid sequence of the corresponding protein has furthermore been derived from the present DNA sequence by the methods described above. The resulting amino acid sequence of the sahH gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. they are of neutral function.

It is furthermore known that changes at the N and/or C terminus of a protein must not substantially impair and may even stabilize the function thereof. Information in this context can be found in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approx. 50° C.–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50° C.–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50° C. to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce amino acids in an improved manner after over-expression of the sahH gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative amino acid production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification 0 472 869, in U.S. Pat. No. 4,601,893, in Schwarzer and Pühler (Bio/Technology 9, 84–87 (1991)), in Reinscheid et al. (Applied and Environmental Microbiology 60, 126–132 (1994)), in LaBarre et al. (Journal of Bacteriology 175, 1001–1007 (1993)), in patent application WO 96/15246, in Malumbres et al. (Gene 134, 15–24 (1993)), in Japanese Laid-Open Specification JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, for enhancement the sahH gene according to the invention was over-expressed with the aid of episomal plasmids. Suitable plasmids are those which are replicated in coryneform bacteria. Numerous known plasmid vectors, such as e.g. pZ1 (Menkel et al., Applied and Environmental Microbiology (1989) 64: 549–554), pEKEx1 (Eikmanns et al., Gene 102:93–98 (1991)) or pHS2–1 (Sonnen et al., Gene 107:69–74 (1991)) are based on the cryptic plasmids pHM1519, pBL1 or pGA1. Other plasmid vectors, such as those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically E. coli), but not in C. glutamicum. Possible vectors are, for example, pSUP301 (Simon et al., Bio/Technology 1, 784–791 (1983)), pK18mob or pK19mob (Schäfer et al., Gene 145, 69–73 (1994)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)), pEM1 (Schrumpf et al, 1991, Journal of Bacteriology 173:4510–4516) or pBGS8 (Spratt et al., 1986, Gene 41: 337–342). The plasmid vector which contains the gene to be amplified is then transferred into the desired strain of C. glutamicum by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of L-amino acids to enhance, in particular over-express, one or more enzymes of the particular biosynthesis pathway, of glycolysis, of anaplerosis, of the citric acid cycle, of the pentose phosphate cycle, of amino acid export and optionally regulatory proteins, in addition to the sahH gene.

Thus, for the preparation of L-amino acids, in addition to enhancement of the sahH gene, one or more genes chosen from the group consisting of the dapA gene which codes for dihydrodipicolinate synthase (EP-B 0 197 335), the gap gene which codes for glyceraldehyde 3-phosphate dehydrogenase (Eikmanns (1992), Journal of Bacteriology 174:6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the zwf gene which codes for glucose 6-phosphate dehydrogenase (JP-A-09224661), the pyc gene which codes for pyruvate carboxylase (DE-A-198 31 609), the mqo gene which codes for malate-quinone oxidoreductase (Molenaar et al., European Journal of Biochemistry 254, 395–403 (1998)), the lysC gene which codes for a feed-back resistant aspartate kinase (Accession No.P26512), the lysE gene which codes for lysine export (DE-A-195 48 222), the hom gene which codes for homoserine dehydrogenase (EP-A 0131171), the ilvA gene which codes for threonine dehydratase (Möckel et al., Journal of Bacteriology (1992) 8065–8072)) or the ilvA(Fbr) allele which codes for a "feed back resistant" threonine dehydratase (Möckel et al., (1994) Molecular Microbiology 13: 833–842), the ilvBN gene which codes for acetohydroxy-acid synthase (EP-B 0356739), the ilvD gene which codes for dihydroxy-acid dehydratase (Sahm and Eggeling (1999) Applied and Environmental Microbiology 65: 1973–1979), the zwa1 gene which codes for the Zwa1 protein (DE: 19959328.0, DSM 13115), can be enhanced, in particular over-expressed.

It may furthermore be advantageous for the production of L-amino acids, in addition to the enhancement of the sahH gene, for one or more genes chosen from the group consisting of:

the pck gene which codes for phosphoenol pyruvate carboxykinase (DE 199 50 409.1; DSM 13047)

the pgi gene which codes for glucose 6-phosphate isomerase (U.S. Ser. No. 09/396,478; DSM 12969), the poxB gene which codes for pyruvate oxidase (DE: 1995 1975.7; DSM 13114), the zwa2 gene which codes for the Zwa2 protein (DE: 19959327.2, DSM 13113) to be attenuated, in particular for the expression thereof to be reduced.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 50%, 0 to 25%, 0 to 10% or 0 to 5% of the activity or concentration of the wild-type protein.

In addition to over-expression of the sahH gene it may furthermore be advantageous for the production of amino acids to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of amino acids. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Organic and inorganic sulfur-containing compounds, such as, for example, sulfides, sulfites, sulfates and thiosulfates, can be used as a source of sulfur, in particular for the preparation of methionine.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

The fermentation broths obtained in this way, in particular containing L-methionine, usually have a dry weight of 7.5 to 25 wt. % and contain L-methionine. It is furthermore also advantageous if the fermentation is conducted in a sugar-limited procedure at least at the end, but in particular over at least 30% of the duration of the fermentation. That is to say, the concentration of utilizable sugar in the fermentation medium is reduced to $\geq 0$ to 3 g/l during this period.

The fermentation broth prepared in this manner, in particular containing L-methionine, is then further processed. Depending on requirements all or some of the biomass can be removed from the fermentation broth by separation methods, such as centrifugation, filtration, decanting or a combination thereof, or left completely in it. This broth is then thickened or concentrated by known methods, such as with the aid of a rotary evaporator, thin film evaporator, falling film evaporator, by reverse osmosis, or by nanofiltration. This concentrated fermentation broth can then be worked up by methods of freeze drying, spray drying, spray granulation or by other processes to give a preferably free-flowing, finely divided powder.

This free-flowing, finely divided powder can then in turn by converted by suitable compacting or granulating processes into a coarse-grained, readily free-flowing, storable and largely dust-free product. In the granulation or compacting it is advantageous to employ conventional organic or inorganic auxiliary substances or carriers, such as starch, gelatin, cellulose derivatives or similar substances, such as are conventionally used as binders, gelling agents or thickeners in foodstuffs or feedstuffs processing, or further substances, such as, for example, silicas, silicates or stearates.

"Free-flowing" is understood as meaning powders which flow unimpeded out of the vessel with the opening of 5 mm (millimeters) of a series of glass outflow vessels with outflow openings of various sizes (Klein, Seifen, Öle, Fette, Wachse 94, 12 (1968)).

As described here, "finely divided" means a powder with a predominant content (>50%) having a particle size of 20 to 200 $\mu$m diameter. "Coarse-grained" means products with a predominant content (>50%) having a particle size of 200 to 2000 $\mu$m diameter. In this context, "dust-free" means that the product contains only small contents (<5%) having particle sizes of less than 20 $\mu$m diameter. The particle size determination can be carried out with methods of laser diffraction spectrometry. The corresponding methods are described in the textbook on "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, Verlag Wiley & Sons (1998).

"Storable" in the context of this invention means a product which can be stored for up to 120 days, preferably up to 52 weeks, particularly preferably 60 months, without a substantial loss (<5%) of methionine occurring.

Alternatively, however, the product can be absorbed on to an organic or inorganic carrier substance which is known and conventional in feedstuffs processing, for example, silicas, silicates, grits, brans, meals, starches, sugars or others, and/or mixed and stabilized with conventional thickeners or binders. Use examples and processes in this context are described in the literature (Die Mühle+ Mischfuttertechnik 132 (1995) 49, page 817).

Finally, the product can be brought into a state in which it is stable to digestion by animal stomachs, in particular the stomach of ruminants, by coating processes ("coating") using film-forming agents, such as, for example, metal carbonates, silicas, silicates, alginates, stearates, starches, gums and cellulose ethers, as described in DE-C-4100920.

If the biomass is separated off during the process, further inorganic solids, for example added during the fermentation, are in general removed. In addition, the animal feedstuffs additive according to the invention comprises at least the predominant proportion of the further substances, in particular organic substances, which are formed or added and are present in solution in the fermentation broth, where these have not been separated off by suitable processes.

In one aspect of the invention, the biomass can be separated off to the extent of up to 70%, preferably up to 80&, preferably up to 90%, preferably up to 95%, and particularly preferably up to 100%. In another aspect of the invention, up to 20% of the biomass, preferably up to 15%, preferably up to 10%, preferably up to 5%, particularly preferably no biomass is separated off.

These organic substances include organic by-products which are optionally produced, in addition to the L-methionine, and optionally discharged by the microorganisms employed in the fermentation. These include L-amino acids chosen from the groups consisting of L-lysine, L-valine, L-threonine, L-alanine or L-tryptophan. They include vitamins chosen from the group consisting of vitamin B1 (thiamine), vitamin B2 (riboflavin), vitamin B5 (pantothenic acid), vitamin B6 (pyridoxine), vitamin B12 (cyanocobalamin), nicotinic acid/nicotinamide and vitamin E (tocopherol). They also include organic acids which carry one to three carboxyl groups, such as, acetic acid, lactic acid, citric acid, malic acid or fumaric acid. Finally, they also include sugars, for example, trehalose. These compounds are optionally desired if they improve the nutritional value of the product.

These organic substances, including L-methionine and/or D-methionine and/or the racemic mixture D,L-methionine, can also be added, depending on requirements, as a concentrate or pure substance in solid or liquid form during a suitable process step. These organic substances mentioned can be added individually or as mixtures to the resulting or concentrated fermentation broth, or also during the drying or granulation process. It is likewise possible to add an organic substance or a mixture of several organic substances to the fermentation broth and a further organic substance or a further mixture of several organic substances during a later process step, for example granulation.

The product described above is suitable as a feedstuffs additive, i.e. feed additive, for animal nutrition.

The L-methionine content of the animal feedstuffs additive is conventionally 1 wt. % to 80 wt. %, preferably 2 wt. % to 80 wt. %, particularly preferably 4 wt. % to 80 wt. %, and very particularly preferably 8 wt. % to 80 wt. %, based on the dry weight of the animal feedstuffs additive. Contents of 1 wt. % to 60 wt. %, 2 wt. % to 60 wt. %, 4 wt. % to 60 wt. %, 6 wt. % to 60 wt. %, 1 wt. % to 40 wt. %, 2 wt. % to 40 wt. % or 4 wt. % to 40 wt. % are likewise possible. The water content of the feedstuffs additive is conventionally up to 5 wt. %, preferably up to 4 wt. %, and particularly preferably less than 2 wt. %.

The invention also provides a process for the preparation of an L-methionine-containing animal feedstuffs additive from fermentation broths, which comprises the steps a) culture and fermentation of an L-methionine-producing microorganism in a fermentation medium;

b) removal of water from the L-methionine-containing fermentation broth (concentration);

c) removal of an amount of 0 to 100 wt. % of the biomass formed during the fermentation; and d) drying of the fermentation broth obtained according to a) and/or b) to obtain the animal feedstuffs additive in the desired powder or granule form.

If desired, one or more of the following steps can furthermore be carried out in the process according to the invention:

e) addition of one or more organic substances, including L-methionine and/or D-methionine and/or the racemic mixture D,L-methionine, to the products obtained according to a), b) and/or c);

f) addition of auxiliary substances chosen from the group consisting of silicas, silicates, stearates, grits and bran to the substances obtained according to a) to d) for stabilization and to increase the storability; or g) conversion of the substances obtained according to a) to e) into a form stable to an animal stomach, in particular rumen, by coating with film-forming agents.

Methods for the determination of L-amino acids are known from the prior art. The analysis can thus be carried out, for example, as described by Spackman et al. (Analytical Chemistry, 30, (1958), 1190) by ion exchange chromatography with subsequent ninhydrin derivation, or it can be carried out by reversed phase HPLC, for example as described by Lindroth et al. (Analytical Chemistry (1979) 51: 1167–1174).

The process according to the invention is used for fermentative preparation of amino acids.

The present invention is explained in more detail in the following with the aid of embodiment examples.

The following microorganism was deposited as a pure culture on May 18, 2001 at the Deutsche Sammlung für Mikroorganismen und Zellkulturen (DSMZ=German Collection of Microorganisms and Cell Cultures, Braunschweig, Germany) in accordance with the Budapest Treaty:

*Escherichia coli* DH5αmcr/pEC-XK99sahHa1ex as DSM 14316.

The isolation of plasmid DNA from *Escherichia coli* and all techniques of restriction, Klenow and alkaline phosphatase treatment were carried out by the method of Sambrook et al. (Molecular Cloning. A Laboratory Manual (1989) Cold Spring Harbor Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

EXAMPLE 1
Preparation of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector SuperCos1 (Wahl et al. (1987) Proceedings of the National Academy of Sciences USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 mg/l ampicillin. After incubation overnight at 37° C., recombinant individual clones were selected.

EXAMPLE 2
Isolation and Sequencing of the sahH Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, Holland, Product Description Zero Background Cloning Kit, Product No. K2500-01), was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the *E. coli* strain DH5αMCR (Grant, 1990, Proceedings of the National Academy of Sciences U.S.A., 87:4645–4649) and plated out on LB agar (Lennox, 1955, Virology, 1:190) with 50 mg/l zeocin.

The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/ Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZerol derivatives were assembled to a continuous contig. The computer-assisted coding region analysis was prepared with the XNIP program (Staden, 1986, Nucleic Acids Research, 14:217–231).

The resulting nucleotide sequence is shown in SEQ ID No. 1. Analysis of the nucleotide sequence showed an open reading frame of 1497 base pairs, which was called the sahH gene. The sahH gene codes for a protein of 498 amino acids.

EXAMPLE 3

Preparation of a Shuttle Expression Vector pEC-XK99EsahHex for Enhancement of the sahH Gene in C. glutamicum 3.1 Cloning of the sahH Gene From the strain ATCC 13032, chromosomal DNA is isolated by the method of Eikmanns et al. (Microbiology 140: 1817–1828 (1994)). On the basis of the sequence of the sahH gene known for C. glutamicum from example 2, the following oligonucleotides were chosen for the polymerase chain reaction (see SEQ ID No. 3 and SEQ ID No. 4):
sahHex1:
5' gt ggt acc-ttc ggt gtc cac tcc aac at 3'
sahHex2:
5' ca tct aga-tag gcg ctg tcg gtg agg tc 3'

The primers shown were synthesized by MWG-Biotech AG (Ebersberg, Germany) and the PCR reaction was carried out by the standard PCR method of Innis et al. (PCR protocols. A guide to methods and applications, 1990, Academic Press) with Pwo-Polymerase from Roche Diagnostics GmbH (Mannheim, Germany). With the aid of the polymerase chain reaction, the primers allow amplification of a DNA fragment approx. 1.7 kb in size, which carries the sahH gene. Furthermore, the primer sahHex1 contains the sequence for the cleavage site of the restriction endonuclease Kpn1, and the primer sahHex2 the cleavage site of the restriction endonuclease XbaI, which are marked by underlining in the nucleotide sequence shown above.

The sahH fragment approx. 1.7 kb in size was cleaved with the restriction endonucleases KpnI and XbaI and then isolated from the agarose gel with the QiaExII Gel Extraction Kit (Product No. 20021, Qiagen, Hilden, Germany).

3.2 Construction of the Shuttle Vector pEC-XK99E

The E. coli-C. glutamicum shuttle vector pEC-XK99E was constructed according to the prior art. The vector contains the replication region rep of the plasmid pGA1 including the replication effector per (U.S. Pat. No. 5,175,108; Nesvera et al., Journal of Bacteriology 179, 1525–1532 (1997)), the kanamycin resistance gene aph(3')-IIa from Escherichia coli (Beck et al. (1982), Gene 19: 327–336), the replication origin of the trc promoter, the termination regions T1 and T2, the lacI$^q$ gene (repressor of the lac operon of E. coli) and a multiple cloning site (mcs) (Norrander, J. M. et al. Gene 26, 101–106 (1983)) of the plasmid pTRC99A (Amann et al. (1988), Gene 69: 301–315).

The E. coli-C. glutamicum shuttle vector pEC-XK99E constructed was transferred into C. glutamicum DSM5715 by means of electroporation (Liebl et al., 1989, FEMS Microbiology Letters, 53:299–303). Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology, 144, 915–927), cleaved with the restriction endonuclease HindIII, and the plasmid was checked by subsequent agarose gel electrophoresis.

Figure 1:
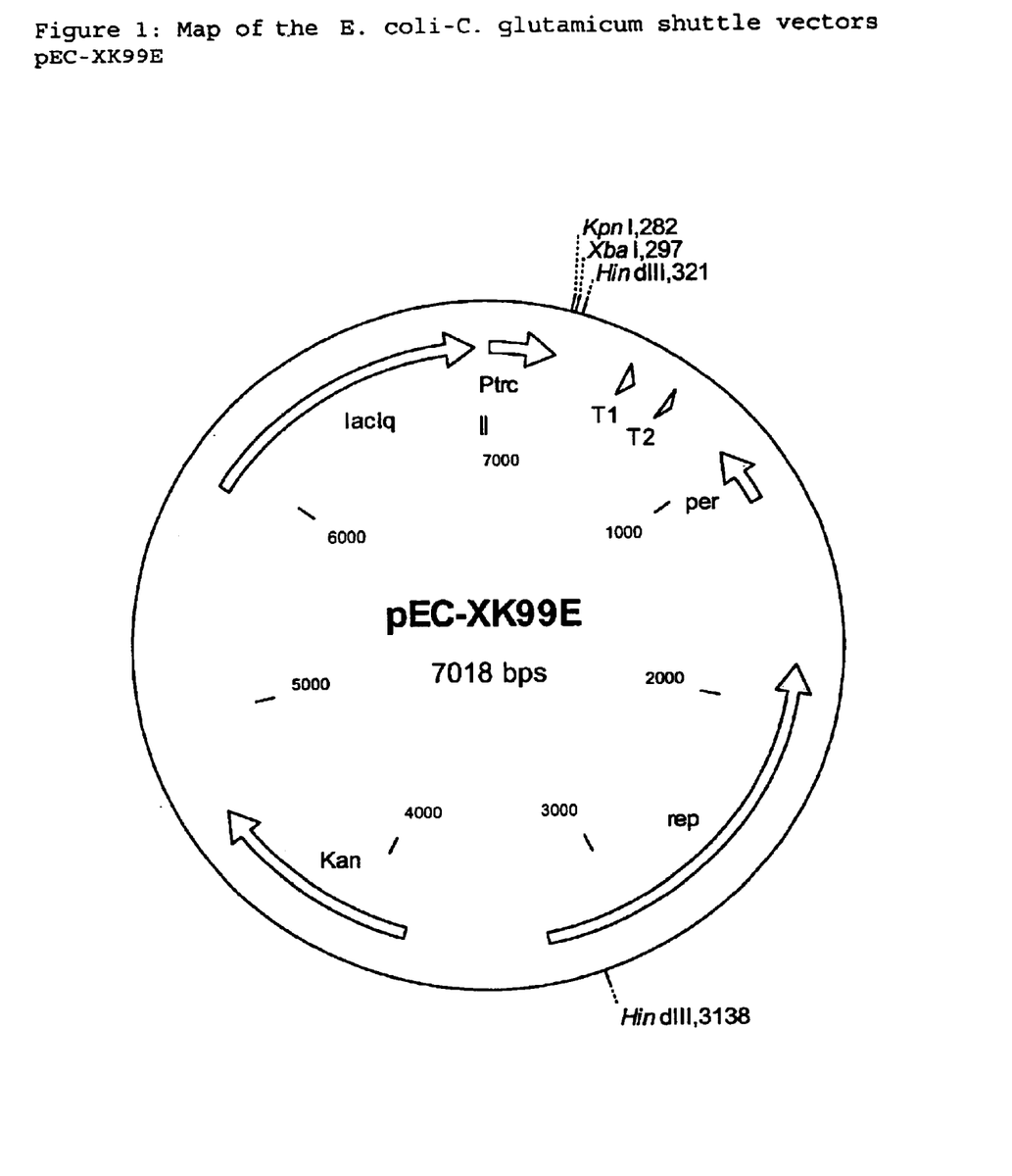
FIG. 1 shows shuttlevector pEC-SK99E.

The plasmid construct obtained in this way was called pEC-XK99E (FIG. 1). The strain obtained by electroporation of the plasmid pEC-XK99E in the C. glutamicum strain DSM5715 was called DSM5715/pEC-XK99E and deposited as DSM13455 at the Deutsche Sammlung für Mikroorganismen und Zellkulturen (DSMZ=German Collection of Microorganisms and Cell Cultures, Braunschweig, Germany) in accordance with the Budapest Treaty.

3.3 Cloning of sahH in the E. coli-C. glutamicum Shuttle Vector pEC-XK99E

The E. coli-C. glutamicum shuttle vector pEC-XK99E described in example 3.2 was used as the vector. DNA of this plasmid was cleaved completely with the restriction enzymes KpnI and XbaI and then dephosphorylated with shrimp alkaline phosphatase (Roche Diagnostics GmbH, Mannheim, Germany, Product Description SAP, Product No. 1758250).

Figure 2:
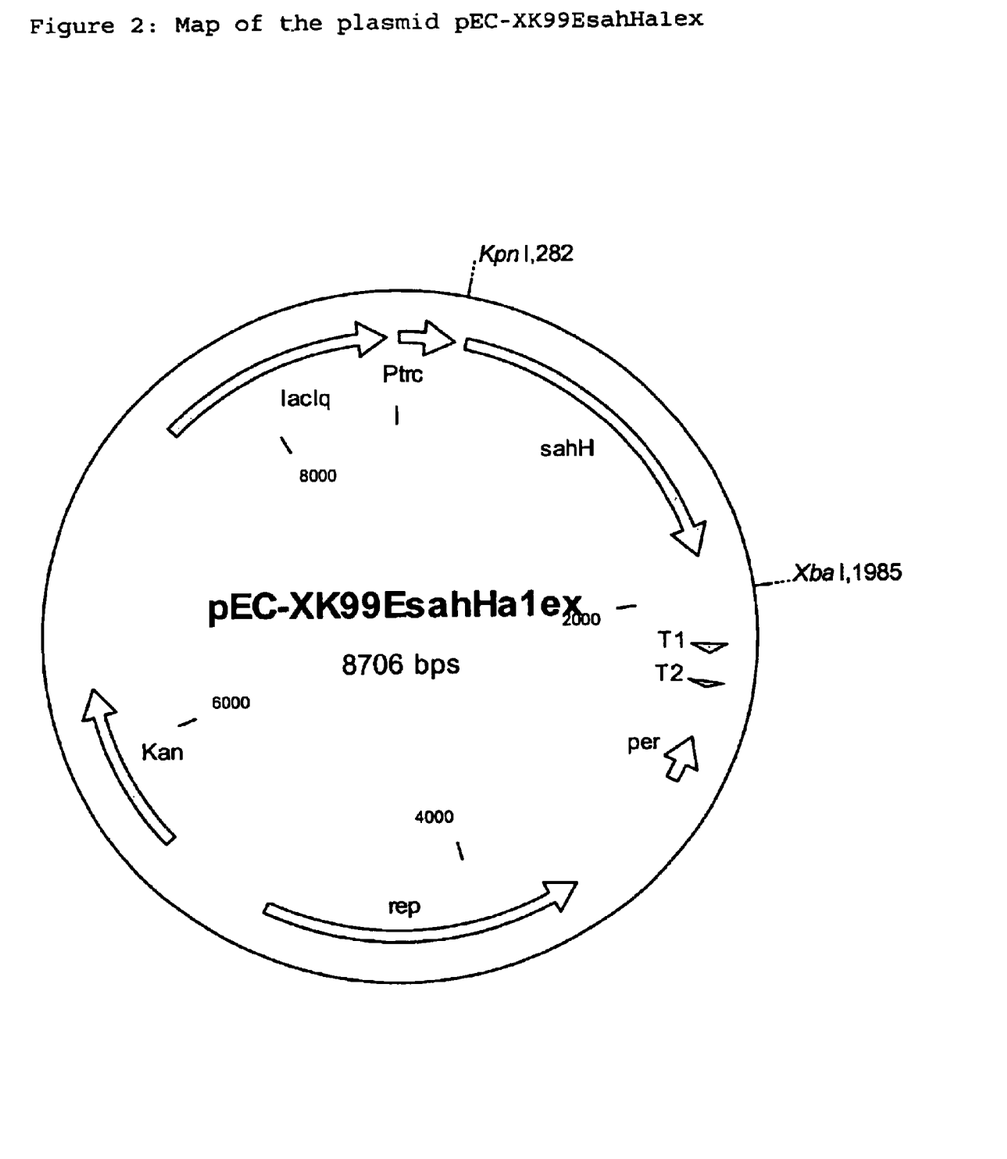
FIG. 2 shows plasmid pEC-XK99Esahtalex.

The sahH fragment 1.7 kb in size described in example 3.1, obtained by means of the PCR and restricted with the restriction endonucleases KpnI and XbaI was mixed with the vector pEC-XK99E prepared and the batch was treated with T4 DNA ligase (Amersham Pharmacia, Freiburg, Germany, Product Description T4-DNA-Ligase, Code no.27-0870-04). The ligation batch was transformed in the E. coli strain DH5αmcr (Hanahan, In: DNA cloning. A practical approach. Vol. I. IRL-Press, Oxford, Washington D.C., USA). Selection of plasmid-carrying cells was made by plating out the transformation batch on LB agar (Lennox, 1955, Virology, 1:190) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzymes KpnI and XbaI to check the plasmid by subsequent agarose gel electrophoresis. The resulting plasmid was called pEC-XK99EsahHa1ex. It is shown in FIG. 2.

EXAMPLE 4

Transformation of the Strain DSM5715 with the Plasmid pEC-XK99EsahHHalex

The strain DSM5715 was transformed with the plasmid pEC-XK99EsahHalex using the electroporation method described by Liebl et al., (FEMS Microbiology Letters, 53:299–303 (1989)). Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology, 144, 915–927), cleaved with the restriction endonucleases KpnI and XbaI, and the plasmid was checked by subsequent agarose gel electrophoresis. The strain obtained was called DSM5715/pEC-XK99EsahHex1.

EXAMPLE 5
Preparation of Lysine

The *C. glutamicum* strain DSM5715/pEC-XK99EsahHalex obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l)) for 24 hours at 33° C. Starting from this agar plate culture, a preculture was seeded (10 ml medium in a 100 ml conical flask). The complete medium CgIII was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |

The pH was brought to pH 7.4

Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1. Medium MM was used for the main culture.

Medium MM

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing is carried out in a 10 ml volume in a 100 ml conical flask with baffles. Kanamycin (25 mg/l) was added. Culturing was carried out at 33° C. and 80% atmospheric humidity.

After 48 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivation with ninhydrin detection.

The result of the experiment is shown in table 1.

TABLE 1

| Strain | OD (660 nm) | Lysine HCl g/l |
|---|---|---|
| DSM5715 | 11.3 | 13.02 |
| DSM5715/pEC-XK99EsahHalex | 12 | 13.57 |

BRIEF DESCRIPTION OF THE FIGURES

FIG. 1: Map of the plasmid pEC-XK99E.

FIG. 2: Map of the plasmid pEC-XK99EsahHalex.

The abbreviations and designations used have the following meaning.

| | |
|---|---|
| Kan: | Kanamycin resistance gene aph(3')-IIa from *Escherichia coli* |
| HindIII | Cleavage site of the restriction enzyme HindIII |
| XbaI | Cleavage site of the restriction enzyme XbaI |
| KpnI | Cleavage site of the restriction enzyme KpnI |
| Ptrc | trc promoter |
| T1 | Termination region T1 |
| T2 | Termination region T2 |
| per | Replication effector per |
| rep | Replication region rep of the plasmid pGA1 |
| lacIq | lacIq repressor of the lac operon of *Escherichia coli* |
| SahH | Cloned sahH gene |

This disclosure is based on priority documents DE 100 44 706.6, DE 101 09 685.2 and U.S. 60/294,277, each incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. An isolated polynucleotide
   which is at least 90% identical to SEQ ID NO: 1, or to a fragment of SEQ ID NO: 1, and
   which encodes a polypeptide having the enzymatic activity of adenosyl homocysteinase.
2. The isolated polynucleotide of claim 1, which is at least 95% identical to SEQ ID NO: 1.
3. The isolated polynucleotide of claim 1, which encodes the polypeptides of SEQ ID NO: 2.
4. The isolated polynucleotide of claim 1, which comprises nucleotides 227 to 1720 of SEQ ID NO: 1.
5. The isolated polynucleotide of claim 1, further comprising at least one promoter, ribosome binding site, regulatory region or expression cassette.
6. The isolated polynucleotide of claim 1, which is RNA.
7. A vector comprising the isolated polynucleotide of claim 1.
8. A vector comprising the isolated polynucleotide of claim 3.
9. A vector comprising the isolated polynucleotide of claim 5.
10. A host cell comprising at least one copy of the isolated polynucleotide of claim 1.
11. A host cell comprising multiple copies of the isolated polynucleotide of claim 1.
12. The host of claim 10, which is a coryneform bacterium.
13. The host cell of claim 10, which is *Corynebacterium glutamicum*.
14. A process for making an amion acid comprising:
    culturing the host cell of claim 10 for a time and under conditions suitable for the production of said amino acid, and
    recovering said amino acid.
15. The process of claim 14, wherein said amino acid is lysine.
16. The process of claim 14, wherein said amino acid is methionine.
17. The process of claim 14, wherein said amino acid is lysine or methionine, and said host cell is a coryneform microorganism, which compared to an unmodified starting strain:
    (A) over-expresses one or more of the following genes:
        the dapA gene which codes for dihydrodipicolinate synthase,
        the gap gene which codes for glyceraldehyde 3-phosphate dehydrogenase,
        the tpi gene which codes for triose phosphate isomerase,
        the pgk gene which codes for 3-phosphoglycerate kinase,
        the zwf gene which codes for glucose 6-phophate dehydrogenase,
        the pyc gene which codes for pyruvate carboxylase,
        the mqo gene which codes for malate-quione oxidoreductase,
        the lysC gene which codes for a feed-back resistant aspartate kinase,
        the lysE gene which codes for lysine export,
        the hom gene which codes for homoserine dehydrogenase
        the ilvA gene which codes for threonine dehydratase or the ilvA (Fbr) allele which codes for a feed back resistant threonine dehydratase,
        the ilvBN gene which codes for acetohydroxy-acid synthase,
        the ilvD gene which codes for dihydroxy-acid dehydratase, or
        the zwa1 gene which codes for the Zwa1 protein; and/or (B) reduces or eliminates the expression of one or more of the following gene(s):
the pck gene which codes for phosphoenol pyruvate carboxykinase,
the pgi gene which codes for glucose 6-phosphate isomerase,
the poxB gene which codes for pyruvate oxidase or
the zwa2 gene which codes for the Zwa2 protein.

18. A host cell comprising at least one copy of the isolated polynucleotide of claim 3.

19. A host cell comprising multiple copies of the isolated polynucleotide of claim 3.

20. The host cell of claim 18, which is a coryneform bacterium.

21. The host cell of claim 18, which is *Corynebacterium glutamicum*.

22. A process for making an amino acid comprising:
culturing the host cell of claim 18 for a time and under conditions suitable for the production of said amino acid, and
recovering said amino acid.

23. The process of claim 22, wherein said amino acid is lysine.

24. The process of claim 22, wherein said amino acid is methionine.

25. The process of claim 22, wherein said amino acid is lysine or methionine, and said host cell is a coryneform microorganism, which compared to an unmodified starting strain:
(A) over-expresses one or more of the following genes:
the dapA gene which codes for dihydrodipicolinate synthase,
the gap gene which codes for glyceraldehyde 3-phosphate dehydrogenase,
the tpi gene which codes for triose phosphate isomerase,
the pgk gene which codes for 3-phosphoglycerate kinase,
the zwf gene which codes for glucose 6-phophate dehydrogenase,
the pyc gene which codes for pyruvate carboxylase,
the mqo gene which codes for malate-quione oxidoreductase,
the lysC gene which codes for a feed-back resistant aspartate kinase,
the lysE gene which codes for lysine export,
the hom gene which codes for homoserine dehydrogenase
the ilvA gene which codes for threonine dehydratase or the ilvA (Fbr) allele which codes for a feed back resistant threonine dehydratase,
the ilvBN gene which codes for acetohydroxy-acid synthase,
the ilvD gene which codes for dihydroxy-acid dehydratase, or
the zwa1 gene which codes for Zwa1 protein; and/or
(B) reduces or eliminates the expression of one or more of the following gene(s):
the pck gene which codes for phosphoenol pyruvate carboxykinase,
the pgi gene which codes for glucose 6-phosphate isomerase,
the poxB gene which codes for pyruvated oxidase or
the zwa2 gene which codes for the Zwa2 protein.

26. A host cell comprising at least one copy of the isolated polynucleotide of claim 5.

27. A host cell comprising multiple copies of the isolated polynucleotide of claim 5.

28. The host cell of claim 26, which is a coryneform bacterium.

29. The host cell of claim 26, which is *Corynebacterium glutamicum*.

30. A process for making an amino acid comprising:
culturing the host cell of claim 26 for a time and under conditions suitable for the production of said amino, and
recovering said amino acid.

31. The process of claim 30, wherein said amino acid is lysine.

32. The process of claim 30, wherein said amino acid is methionine.

33. The process of claim 30, wherein said amino acid is lysine or methionine, and said host cell is a coryneform microorganism, which compared to an unmodified starting strain:
(A) over-expresses one or more of the following genes:
the dapA gene which codes for dihydrodipicolinate synthase,
the gap gene which codes for glyceraldehyde 3-phosphate dehydrogenase,
the tpi gene which codes for triose phosphate isomerase,
the pgk gene which codes for 3-phosphoglycerate kinase,
the zwf gene which codes for glucose 6-phophate dehydrogenase,
the pyc gene which codes for pyruvate carboxylase,
the mqo gene which codes for malate-quione oxidoreductase,
the lysC gene which codes for a feed-back resistant aspartate kinase,
the lysE gene which codes for lysine export,
the hom gene which codes for homoserine dehydrogenase
the ilvA gene which codes for threonine dehydratase or the ilvA (Fbr) allele which codes for a feed back resistant threonine dehydratase,
the ilvBN gene which codes for acetohydroxy-acid synthase,
the ilvD gene which codes for dihydroxy-acid dehydratase, or
the zwa1 gene which codes for Zwa1 protein; and/or
(B) reduces or eliminates the expression of one or more of the following gene(s):
the pck gene which codes for phosphonenol pyruvate carboxykinase,
the pgi gene which codes for glucose 6-phosphate isomerase,
the poxB gene which codes for pyruvate oxidase or
the zwa2 gene which codes for the Zwa2 protein.

34. An isolated polynucleotide that encodes a polypeptide which is at least 90% identical to SEQ ID NO: 2, which polypeptide has the enzymatic activity of adenosyl homocysteinase.

35. The isolated polynucleotide of claim 34 that encodes a polypeptide which is at least 95% identical to SEQ ID NO: 2.

36. The isolated polynucleotide of claim 34 that encodes a polypeptide comprising SEQ ID NO: 2.

37. A vector comprising the isolated polynucleotide of claim 34.

38. A host cell comprising the isolated polynucleotide of claim 34.

39. A process for producing an amino acid comprising:
culturing the host cell of claim 38 for a time and under conditions suitable for the production of said amino acid, and
recovering said amino acid.

40. An isolated polynucleotide which hybridizes to the complement of SEQ ID NO: 1 under stringent conditions and which encodes a polypeptide having the enzymatic activity of adenosyl homocysteinase, and wherein stringen conditions comprise washing at a temperature of 68° C. in 2×SSC.

41. A vector comprising the isolated polynucleotide of claim 40.

42. A host cell comprising the isolated polynucleotide of claim 40.

43. A process for producing an amino acid comprising:

culturing the host cell of claim 42 for a time and under conditions suitable for the production to said amino acid, and recovering said amino acid.

44. An isolated polynucleotide consisting of at least 30 consecutive nucleotides of SEQ ID NO:1, or at least 30 consecutive nucleotides of the full complement of SEQ ID NO: 1.

45. An isolated polynucleotide which consists of at least 40 consecutive nucleotides of SEQ ID NO: 1, or at least 40 consecutive nucleotides of the full complement of SEQ ID NO: 1.

46. An isolated polynucleotide which consists of at least 50 consecutive nucleotides of SEQ ID NO: 1, or at least 50 consecutive nucleotides of the full complement of SEQ ID NO: 1.

47. *Escherichia coli* strain DH5αmcr/pEC-XK99sahHa1ex deposited as DSM 14316.

* * * * *